(12) United States Patent
Petersen

(10) Patent No.: US 6,500,187 B1
(45) Date of Patent: *Dec. 31, 2002

(54) SCALPEL WITH A DOUBLE GRIND BLADE EDGE AND DETACHABLE HANDLE

(76) Inventor: Thomas D. Petersen, 9680 Alto Dr., La Mesa, CA (US) 91941

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/258,152

(22) Filed: Feb. 26, 1999

(51) Int. Cl.$^7$ .............................................. A61B 17/32
(52) U.S. Cl. ........................................ 606/167; 30/329
(58) Field of Search ................................. 606/166, 167; 30/2, 151, 335, 329, 332, 336, 337, 338, 339, 342, 343

(56) References Cited

U.S. PATENT DOCUMENTS

| | | | |
|---|---|---|---|
| 2,382,304 A | * 8/1945 | Foltz et al. | |
| 3,311,976 A | * 4/1967 | Matwijcow | 30/335 |
| 4,014,343 A | * 3/1977 | Esty | |
| 4,147,443 A | * 4/1979 | Skobel | 403/267 |
| 4,414,974 A | * 11/1983 | Dotson et al. | 606/167 |
| 4,627,194 A | * 12/1986 | Friel | |
| 4,985,035 A | * 1/1991 | Torre | 606/167 |
| 5,100,391 A | * 3/1992 | Schutte et al. | 606/167 |
| 5,261,922 A | * 11/1993 | Hood | |
| 5,330,493 A | * 7/1994 | Haining | 606/167 |
| 5,342,379 A | * 8/1994 | Volinsky | 606/167 |
| 5,527,329 A | * 6/1996 | Gharibian | 606/167 |
| 5,924,206 A | * 7/1999 | Cote et al. | 30/337 |
| 5,938,676 A | * 8/1999 | Cohn et al. | 606/167 |

OTHER PUBLICATIONS

American V. Mueller "The Surgical Armamentarium", p. 10, (1980).*

* cited by examiner

Primary Examiner—Michael H. Thaler
(74) Attorney, Agent, or Firm—H. Jay Spiegel

(57) ABSTRACT

A scalpel having a blade with a fitting molded about or assembled to its proximal end with the fitting having a proximally facing opening sized to receive an end of a distal portion of a detachable handle. The handle includes a proximal portion designed to be gripped by the surgeon and a distal portion including a male coupling half designed to be received within the proximal opening of the fitting, which proximal opening is configured as a female coupling half. The proximal and distal portions of the handle are angled with respect to one another defining an angle from about 0°–10°. The male coupling half may be inserted within the female coupling half in either one of two diametrically opposed orientations. Thus, due to the angulation between the proximal portion of the handle and the distal portion of the handle, the proximal portion of the handle is either angled downwardly or upwardly with respect to the axis of the blade itself. The handle may be attached to the blade in either one of these two positions depending upon the particular surgical step that is being carried out by the surgeon. The blade itself is provided with a double grind which enhances the sharpness and longetivity of the blade. In the preferred embodiment, the blade includes a primary grind defining an angle of 6°–10° per side and a secondary and final grind of 14°–18° per side. The blade itself is made of a thickness of from 0.020–0.029 inches, and, if desired, the cutting surface of the scalpel blade may be coated with a very thin layer of zirconium nitride or other coating material as disclosed.

11 Claims, 10 Drawing Sheets

SECTION 11

SECTION 14

SECTION 20

SECTION 22

SECTION 23

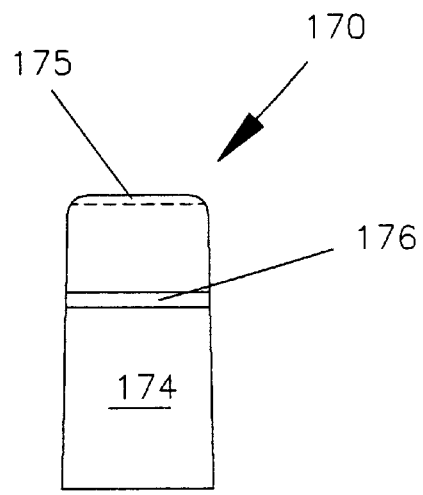
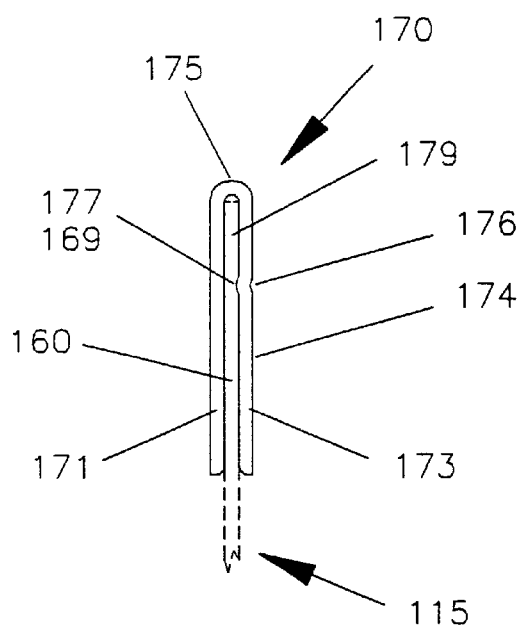
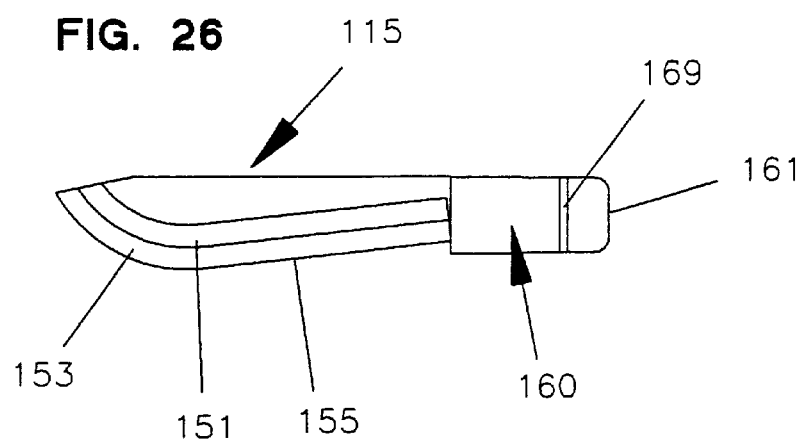

SCALPEL WITH A DOUBLE GRIND BLADE EDGE AND DETACHABLE HANDLE

BACKGROUND OF THE INVENTION

The present invention relates to a scalpel with a double grind blade edge and detachable handle. During performance of surgery, the surgeon typically employs a scalpel to cut tissue. In this environment, the scalpel blade becomes dull within one to two minutes as evidenced by the tearing of tissues with the scalpel blade in jagged, uneven cuts. Eventually, after a total of three to five minutes, the blade will no longer cut tissues and must be replaced.

During a typical total hip or total knee surgery case, the surgeon can use as many as ten to fifteen blades. Having to change the scalpel blade that many times during the course of a single surgery eliminates any notion of continuity and greatly increases surgery time while also increasing the risk that the surgeon or nurse technician will be cut while changing the blade, thereby being exposed to communicable diseases such as AIDS and the various types of hepatitis.

Applicant has found that the necessity to change blades as often as ten to fifteen times per surgery can increase the length of time of the surgery by as much as 15% or more. A typical operating room costs about $1,200.00 per hour to staff and operate. If it were possible to save time during the performance of surgery by devising a scalpel blade that would not have to be changed as often as is currently done, great savings of time and money would result.

Applicant has found that angulation of the blade is helpful when doing certain surgical tasks. For example, it is easier to cut the skin with the blade tilted upward and for certain precise dissection, it is easier when the blade is tilted downward.

Additionally, when human tissue is torn rather than cut, ugly, painful scars result. A blade that would stay sharp for 10–20 minutes would definitely alleviate scarring and subsequent pain to the patient.

Additionally, typical scalpel blades as currently used are extremely thin, typically having a thickness of 0.015 to 0.018 inches with a large oval fixation hole in the tang of the blade. As a result, it is quite common for the scalpel blade tip to break off in the depths of the wound at the surgical site. When this occurs, it is often difficult to find and retrieve the blade tip. When a surgery is completed without retrieval of the blade tip, a malpractice law suit will often result because the unretrieved blade is easily visible in an X-ray image. Thus, also, a need has developed for a scalpel blade that has reduced brittleness and is less likely to break off in use.

It is with these needs in mind that the present invention was developed.

SUMMARY OF THE INVENTION

The present invention relates to a scalpel with double grind blade edge and detachable handle. The present invention includes the following interrelated objects, aspects and features:

(1) In a first embodiment, the present invention contemplates a scalpel having a blade with a fitting molded about the proximal end thereof. The fitting has a proximally facing opening that is sized and configured to receive an end of a distal portion of a detachable handle.

(2) In the first and second embodiments, the handle includes a proximal portion that is designed to be gripped by the surgeon and a distal portion that comprises a male coupling half designed to be received within the proximal opening of the fitting, which proximal opening comprises a female coupling half.

(3) In the first and second embodiments, the proximal and distal portions of the handle are preferably angled with respect to one another with the proximal portion of the handle being angled from about 0°–10° with respect to the axis of the distal portion of the handle. Additionally, the proximal portion of the handle is tapered from a thinner portion adjacent a distal end thereof to a thicker portion adjacent a proximal end thereof. The taper in the distal to proximal direction may be in the range of approximately 1°–2°. The male coupling half at the distal portion of the handle may be inserted within the female coupling half at the proximal end of the blade fitting in either one of two diametrically opposed orientations. Thus, due to the angulation between the proximal portion of the handle and the distal portion of the handle, the proximal portion of the handle is either angled downwardly or upwardly with respect to the axis of the blade itself. Thus, the handle may be attached to the blade in either one of these two positions depending upon the particular surgical step that is being carried out by the surgeon.

(4) In the first and second embodiments, the blade itself is provided with a double grind which enhances the sharpness and longetivity of the blade. In the preferred embodiment, the blade includes a primary grind defining an angle of 6°–10° per side and a secondary and final grind of 14°–18° per side. Thus, as should be understood, the absolute edge of the blade is defined by two angled surfaces defining the final grind of the blade which creates an angle from the edge of the blade backward of 28°–36°.

(5) In a further aspect, in the embodiments of the present invention, the blade itself is made of a thickness of from 0.020–0.029 inches as compared to commonly used scalpel blades which, as explained above, have a thickness of about 0.015–0.018 inches. Additionally, if desired, the cutting surface of the scalpel blade may be coated with a very thin layer of, for example, zirconium nitride by any suitable process such as, for example, vapor deposition. This coating increases the longetivity of the sharpness of the scalpel blade by up to ten times. Other alternative coatings and methods of coating are disclosed herein.

(6) In the second embodiment, instead of molding the fitting about the blade, the fitting is mechanically connected to the blade and may be removed therefrom for sterilization. In the second embodiment, a spring clip is interposed between the proximal end of the blade and the fitting and the blade may be attached to the fitting via the spring clip in either one of two opposed orientations.

(7) Applicant has found that applying a thin coating of body compatible intermetallic nitrides, oxides or carbides to the blade's surface markedly adds to the sharpness and longevity of the blade. Examples of such metal elements are: Titanium, Zirconium, Niobium, Hafnium and Tantalum. Additionally, adding the coatings of body compatible intermetallic phosphides to the blade surface creates a lubricious condition allowing the blade to cut more smoothly through tissues. Examples of such metal elements are: phosphides of Titanium, Zirconium, Niobium, Hafnium, Tantalum and Magnesium (Mg).

Accordingly, it is a first object of the present invention to provide a scalpel with double grind blade edge and detachable handle.

It is a further object of the present invention to provide such a device wherein a handle is receivable in a proximal fitting attached to the scalpel blade in either one of two opposed orientations.

It is a still further object of the present invention to provide such a scalpel with a blade edge defined by a double grind to enhance longetivity of sharpness.

It is a yet further object of the present invention to provide such a scalpel blade of a thickness in the range of 0.020–0.029 inches to enhance strength and significantly reduce the incidence of blade breakage.

It is a still further object of the present invention to provide such a scalpel with a proximal fitting molded about the proximal end of the blade, in one embodiment thereof.

It is a still further object of the present invention to provide such a scalpel with a proximal fitting mechanically connectable to the proximal end of the blade, in a second embodiment thereof.

These and other objects, aspects and features of the present invention will be better understood from the following detailed description of the preferred embodiment when read in conjunction with the appended drawing figures.

BRIEF DESCRIPTION OF THE DRAWINGS

FIG. 24 shows a side view of a spring clip of the second embodiment of the present invention.

FIG. 25 shows a top view of the spring clip of FIG. 24.

FIG. 26 shows a side view of a blade portion in accordance with the second embodiment of the present invention.

SPECIFIC DESCRIPTION OF THE PREFERRED EMBODIMENT

Figure 1:
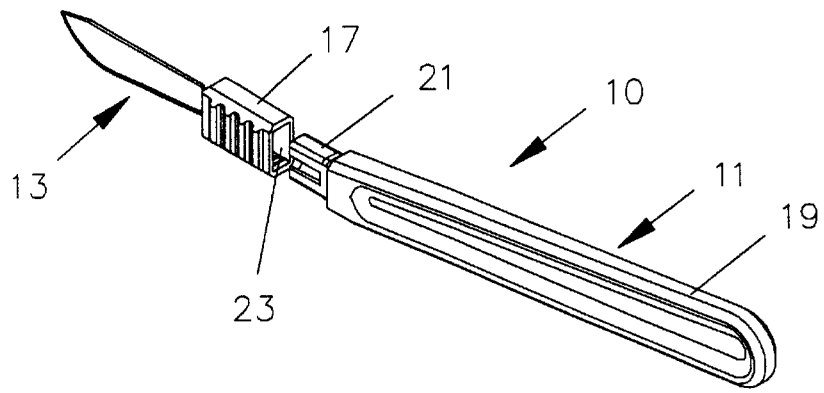
FIG. 1 shows an exploded perspective view of the preferred embodiment of the present invention with the handle in a first orientation with respect to the blade.

With reference, first, to FIGS. 1–15, a scalpel in accordance with the teachings of a first embodiment of the present invention is generally designated by the reference numeral 10 and includes (FIGS. 1–3) a handle 11 and a blade portion 13 consisting of a blade 15 and a proximal fitting 17.

The handle 11 includes a proximal portion 19 and a distal portion 21 consisting of a male half of a coupling. An opening 23 facing in the proximal direction from the proximal fitting 17 of the blade portion 13 comprises a female coupling half sized and configured to receive the male coupling half 21.

Figure 12:
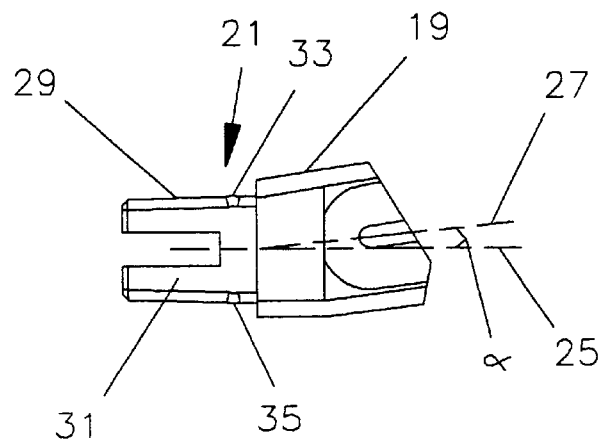
FIG. 12 shows an enlarged perspective view of the distal portion of the handle.

With reference to FIG. 12, it is seen that the male coupling half 21 extends along an axis 25 that makes an angle α with respect to the axis 27 of the proximal portion 19 of the handle. In the preferred embodiment of the present invention, the angle α falls within the range of 0°–10°.

With further reference to FIG. 12, it is seen that the male coupling half 21 includes two vertically spaced tangs 29 and 31. The tang 29 includes a vertically extending "bump" 33 whereas the tang 31 includes a downwardly depending "bump" 35. The bumps 33 and 35 are provided for a purpose to be described in greater detail hereinafter. However, as should be understood from FIG. 12, the male coupling half 21 is symmetrical about the axis 25 such that it may be inserted within the proximally facing opening 23 of the proximal fitting 17 of the blade portion 13 in any one of two diametrically opposed orientations.

Figure 2:
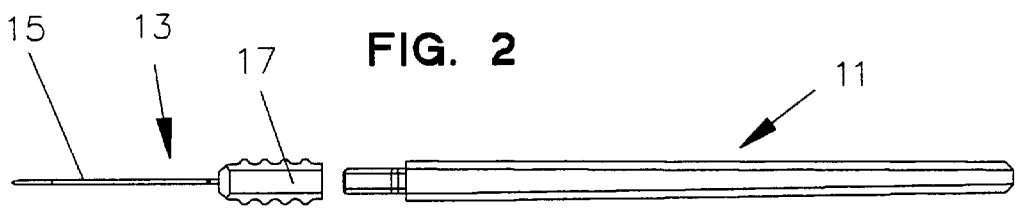
FIG. 2 shows a top view of the configuration of FIG. 1.
Figure 3:
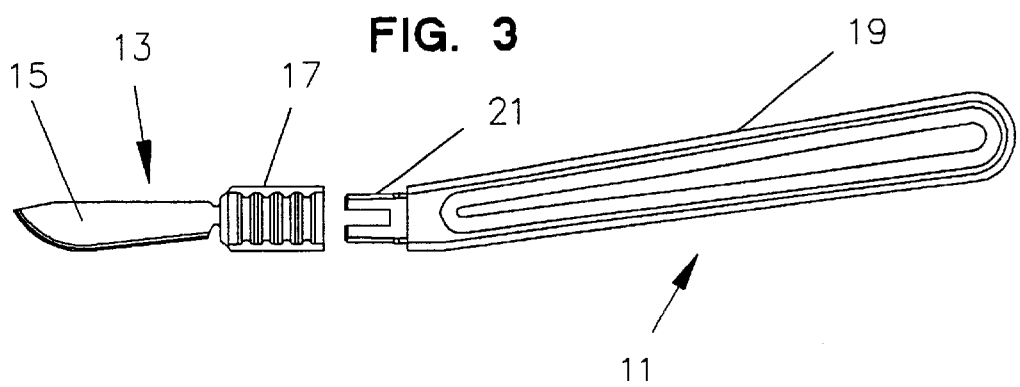
FIG. 3 shows a side view of the configuration of FIGS. 1 and 2.
Figure 4:
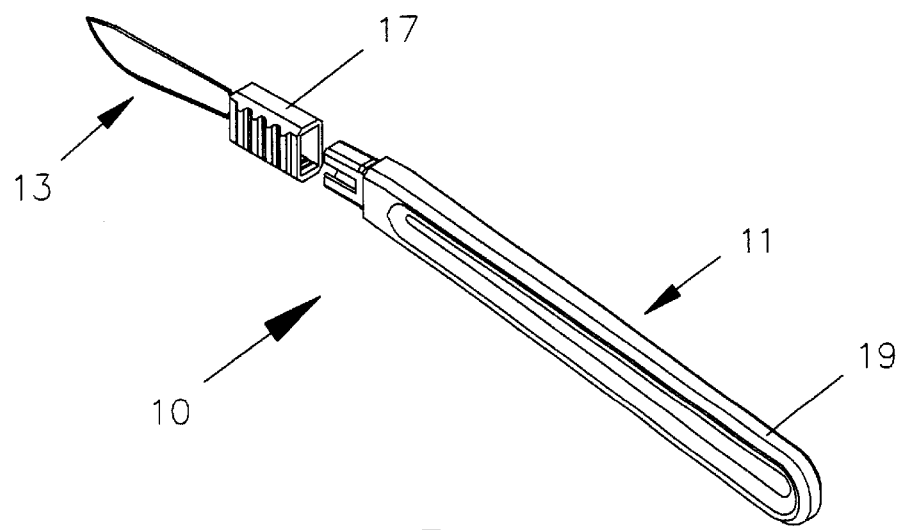
FIG. 4 shows an exploded perspective view of the preferred embodiment of the present invention with the handle rotated about its axis 180° with respect to the orientation shown in FIGS. 13.
Figure 5:
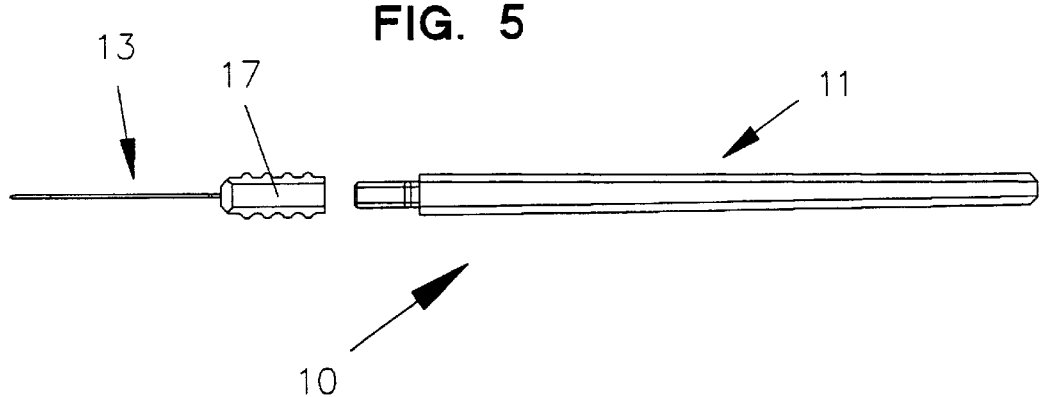
FIG. 5 shows a top view of the orientation of parts shown in FIG. 4.
Figure 6:
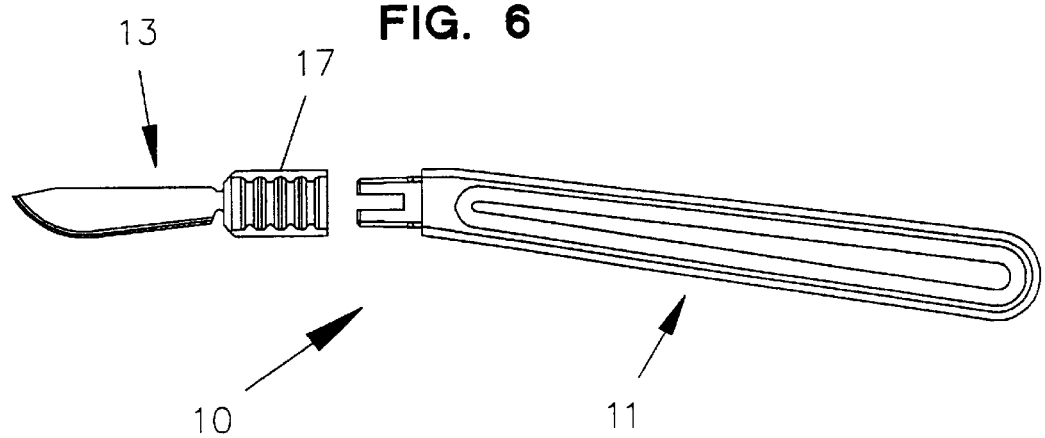
FIG. 6 shows a side view of the orientation of parts of FIGS. 4–5.

In this regard, reference is now made to FIGS. 4–6 which show the identical components as shown in FIGS. 1–3 except that the handle 11 is oriented diametrically opposed to its orientation shown in FIGS. 1–3. As should be understood, looking first at FIG. 3, with the handle 11 in the orientation shown with respect to the blade portion 13, the proximal portion 19 of the handle 11 is angled upwardly with respect to the blade 15. By contrast, with reference to FIG. 6, when the handle 11 is moved to the position shown in FIG. 6, the proximal portion 19 of the handle 11 extends in a downward angle with respect to the blade 15. Thus, the ability to couple the handle 11 to the blade portion 13 in either one of two orientations increases the versatility of the scalpel 10.

Figure 7:
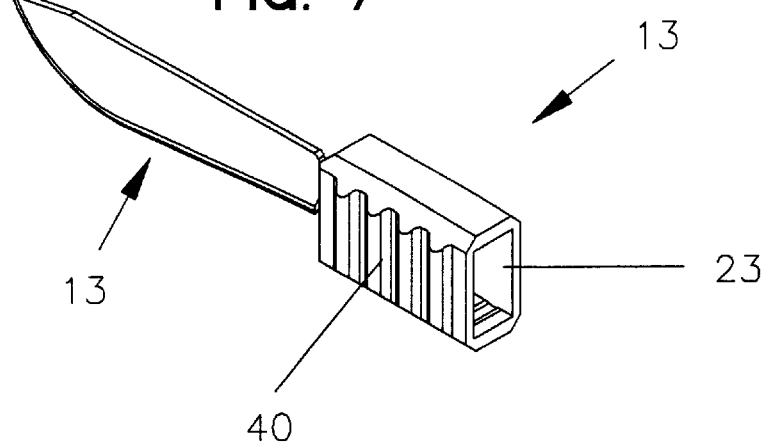
FIG. 7 shows an enlarged perspective view of the blade portion of the present invention.
Figure 8:
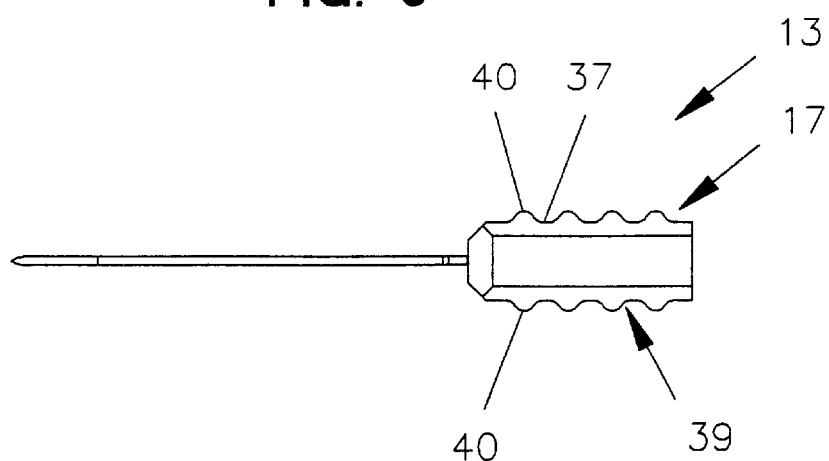
FIG. 8 shows a top view of the blade portion illustrated in FIG. 7.
Figure 9:
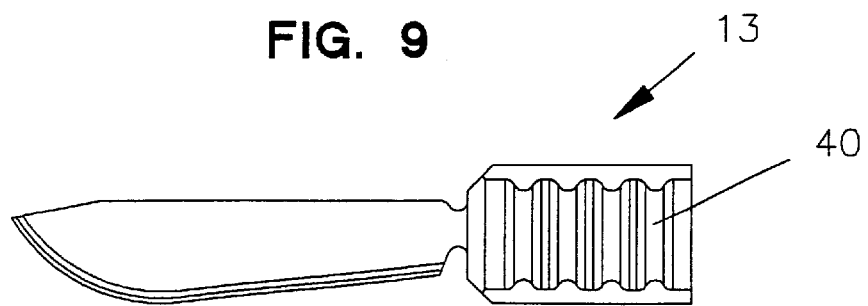
FIG. 9 shows a side view of the blade portion illustrated in FIGS. 7 and 8.

FIGS. 7, 8 and 9 show further details of the blade portion 13. As seen in these figures, the proximal fitting 17 includes sides 37 and 39 that include a plurality of vertically extending ribs 40 that are provided to permit gripping of the fitting 17 by the surgeon. The opening 23 is generally rectangular and has surfaces that correspond to the outer configuration of the tangs 29 and 31 as particularly seen in FIG. 12.

Figure 13:
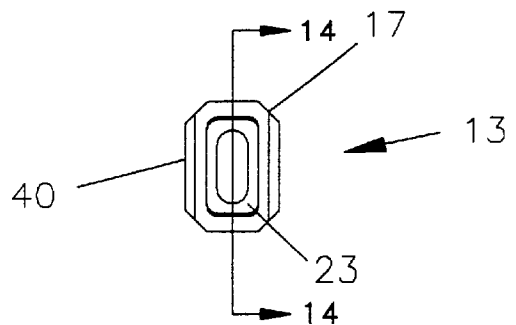
FIG. 13 shows an end view of the proximal end of the blade fitting.
Figure 14:
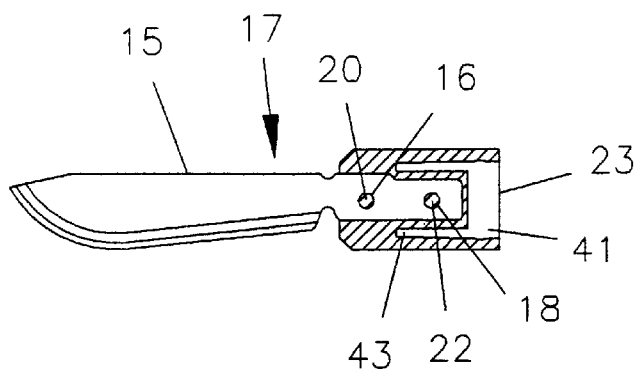
FIG. 14 shows a cross-sectional view along the line 14—14 of FIG. 13.
Figure 15:
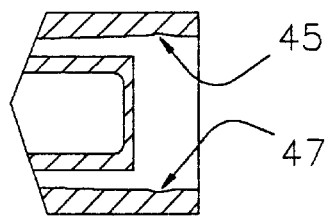
FIG. 15 shows an enlargement of the proximal end of the fitting as shown in FIG. 14.

With reference to FIGS. 13, 14 and 15, additional details of the recess 23 are evident. With particular reference to FIG. 14, it is seen that the recess 23 has a proximal portion 41 and a distal portion 43. The proximal portion 41 is generally rectangular in cross-section and the distal portion 43 comprises a thin, rectangular edge-like chamber conforming, in outer periphery, to the outer peripheries of the distal ends of the tangs 29 and 31 (with reference to FIG. 12), which distal ends are received within the distal portion 43 of the recess 23. With particular reference to FIG. 15, it is seen that the proximal portion 41 of the recess 23 includes two recesses 45 and 47 that are designed to releasably receive the respective bumps 33 and 35 on the male coupling half 21, in one orientation of the handle 11 as seen in FIGS. 1–3, and wherein the recesses 45 and 47 receive the bumps 35 and 33, respectively, when the handle 11 is in the orientation shown in FIGS. 4–6. The interaction between the bumps 33, 35 and the recesses 45, 47, in either orientation of the handle 11 with respect to the blade portion 13 retains the blade portion 13 firmly attached to the handle portion 13 until the surgeon grips the proximal fitting 13 and forceably removes the handle 11 therefrom.

Figure 10:
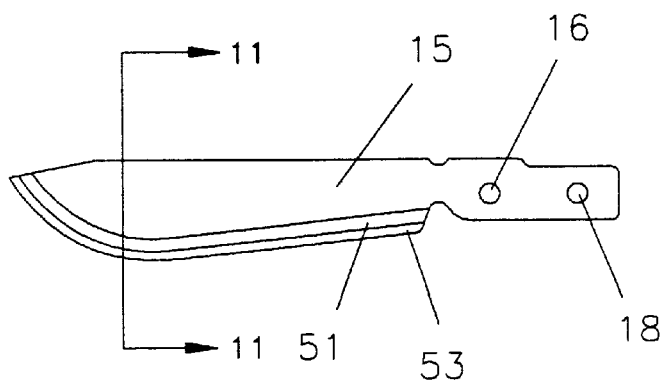
FIG. 10 shows an enlarged side view of the blade itself with the proximal fitting removed to show detail.
Figure 11:
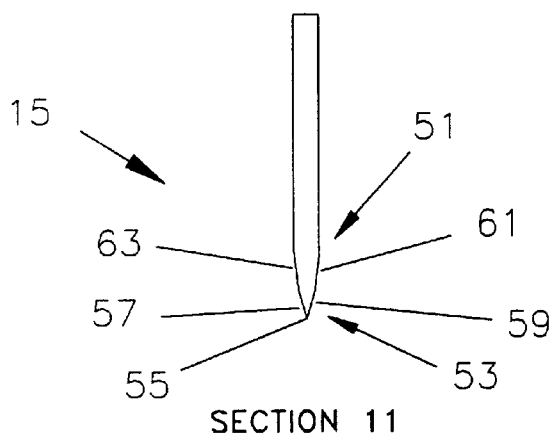
FIG. 11 shows a cross-sectional view along the line 11—11 of FIG. 10.

With particular reference to FIGS. 10 and 11, it is seen that the blade 15 includes a primary grind 51 and a secondary grind 53. As best seen in FIG. 11, the secondary grind 53 terminates at a sharp edge 55. The secondary grind makes an angle between the two surfaces 57 and 59 thereof in the range of 28° to 36°, consisting of an angle of 14°–18° per side 57 or 59. The primary grind 51 is made up of surfaces 61 and 63 that make a total angle, therebetween, of 12° to 20° including 6° to 10° per side. The double grind consisting of the primary grind 51 and the secondary grind 53 have been found to enhance sharpness and longetivity of the blade 15 as compared to prior art blades. An additional factor involves the actual thickness of the blade 15 which, in accordance with the teachings of the present invention, falls within the range of 0.020–0.029 inches in thickness.

If desired, the grinds 51 and 53 and the edge of the blade 15 may be suitably coated with a body compatible very thin layer of intermetallic nitrides, oxides or carbides by any suitable process such as, for example, vapor deposition or controlled brazing techniques.

If desired, the grinds 51 and 53 and the edge 55 of the blade 15 may be suitably coated with a very thin layer of zirconium nitride by any suitable process such as, for example, vapor deposition. Applicant has found that use of such a coating, properly applied, can increase the longetivity of the blade edge 55 by a factor of up to ten times over an uncoated blade.

If desired, the grinds 51 and 53 and the edge of the blade 15 may be suitably coated with a body compatible intermetallic phosphide by any suitable process such as, for example, vapor deposition or controlled brazing techniques. Applicant has found that adding intermetallic phosphides to the blade surface makes the blade more lubricious and that the blade, so coated, cuts more smoothly through the tissues. Intermetallic phosphides suitable for this purpose include phosphides of Titanium, Zirconium, Niobium, Hafnium, Tantalum and Magnesium.

If desired, the male coupling half 21 may be tapered from larger dimensions at the proximal end thereof to smaller dimensions at the distal end thereof and the recess 23 may be correspondingly tapered.

In the first embodiment of the present invention, the proximal fitting 17 is molded or ultrasonically welded about the blade 15. With reference to FIG. 14, it is seen that the blade 15 is provided with two spaced holes 16 and 18 and portions of the fitting 17 designated by the reference numerals 20 and 22 flow over the holes 16 and 18, respectively, during the molding process to thereby fix the blade 15 in the fitting 17. The fitting 17 is preferably made of a suitable molded plastic or metal material. The handle 11 may also be made of the same or similar molded plastic or metal material. Where metal is used, i.e., 17–4 stainless steel, Titanium or Magnesium, a process known as "Metal Injection Molding" is employed.

The blade 15 may be made of any suitable blade material such as, for example, hardened, tempered stainless steel. Alternatively, the blade 15 may be made of a suitable ceramic material.

Where the blade is coated with any of the coatings disclosed herein, in the preferred embodiment, the coating has a thickness of less than 300 nanometers.

If desired, the male coupling half 21 and the recess 23 in the proximal fitting 17 may be made of square cross-sections so that the handle 11 may be attached to the blade portion 13 in any one of four different orientations, including the two orientations illustrated with respect to FIGS. 1–3 and 4–6, respectively, and two additional orientations wherein the angulature of the proximal end 19 of the handle 11 is either to the left or to the right with respect to the plane defining the blade 15.

Figure 16:
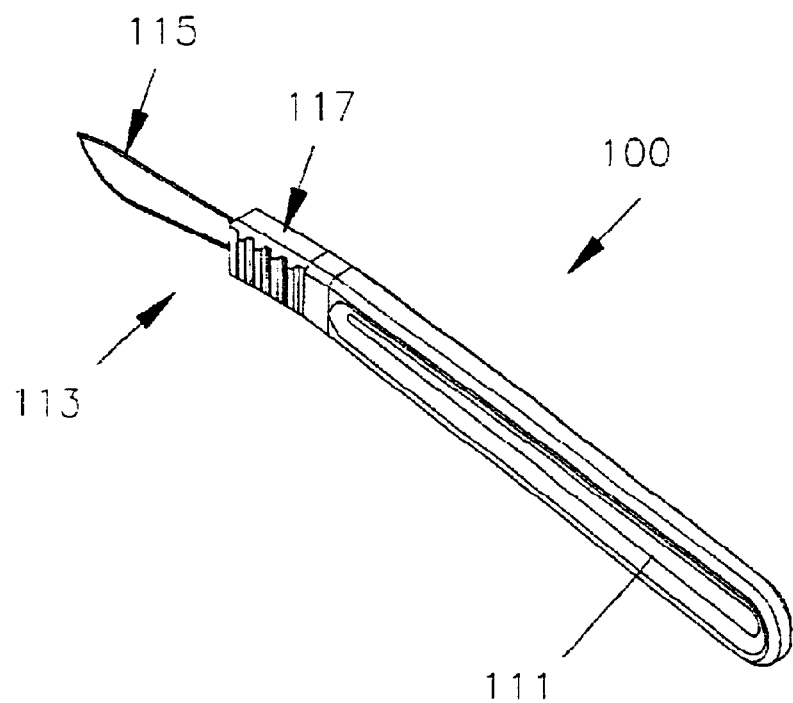
FIG. 16 shows a perspective view of a second embodiment of the present invention.

With reference to FIGS. 16–28, a second embodiment of the present invention is generally designated by the reference numeral 100 and is seen, with particular reference to FIG. 16, to include a handle 111 and a blade portion 113 consisting of a blade 115 and a proximal fitting 117.

Figure 21:
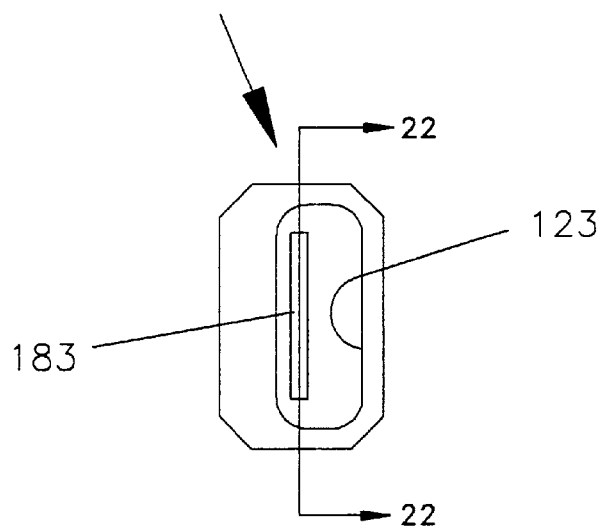
FIG. 21 shows a view looking distally from the proximal end of the proximal fitting of the second embodiment of the present invention.
Figure 22:
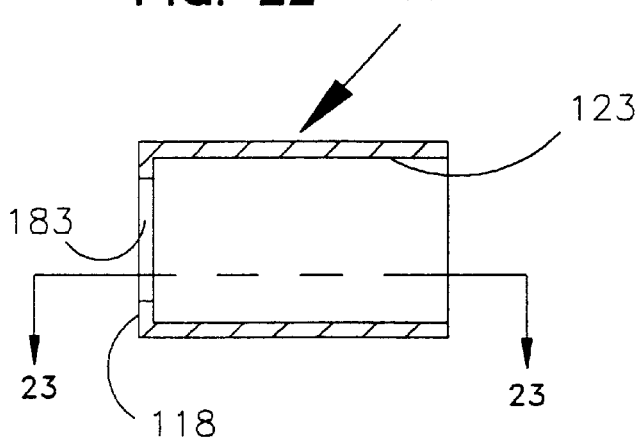
FIG. 22 shows a cross-sectional view along the line 22—22 of FIG. 21.
Figure 23:
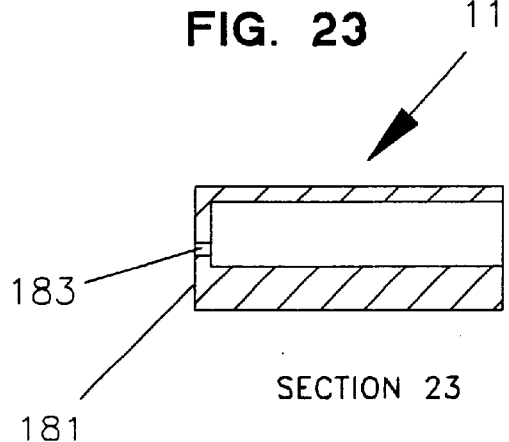
FIG. 23 shows a cross-sectional view along the line 23—23 of FIG. 22.

With reference to FIGS. 17–20, the handle 111 includes a proximal portion 119 and a distal portion 121, consisting of a male half of a coupling. With reference to FIGS. 21 and 22, an opening 123 facing in the proximal direction from the proximal fitting 117 of the blade portion 113 comprises a female coupling half, sized and configured to receive the male coupling half 121.

Figure 17:
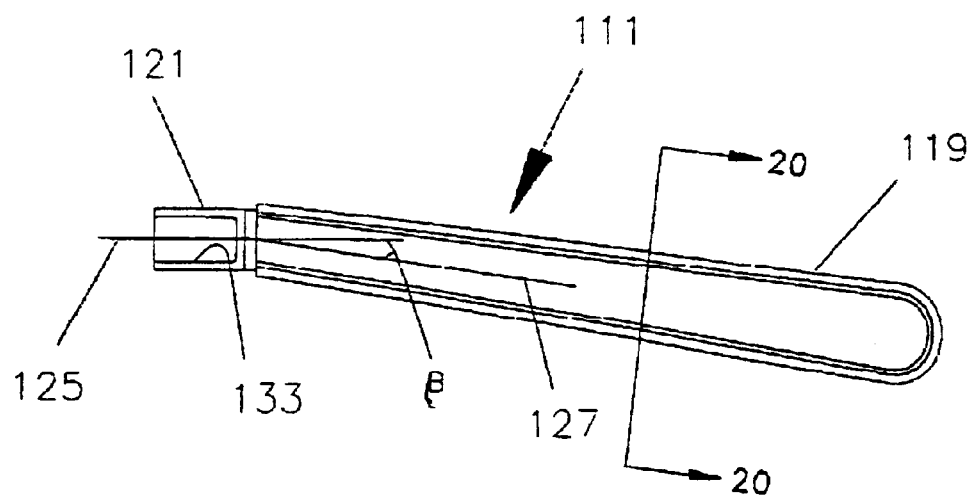
FIG. 17 shows a side view of the handle of the second embodiment.

As best seen in FIG. 17, the male coupling half 121 extends along an axis 125 that makes an angle β with respect to the axis 127 of the proximal portion 119 of the handle 111. As in the case of the first embodiment of the present invention, the angle β preferably falls within the range of 0°–10°.

Figure 18:
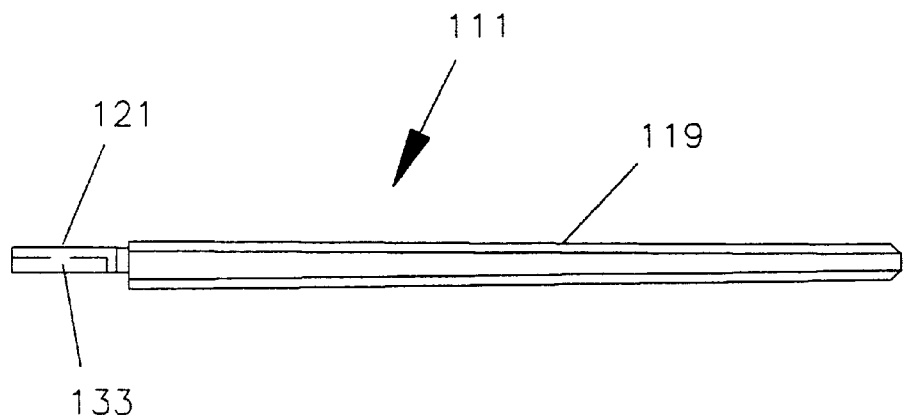
FIG. 18 shows a top view of the handle of FIG. 17.
Figure 19:
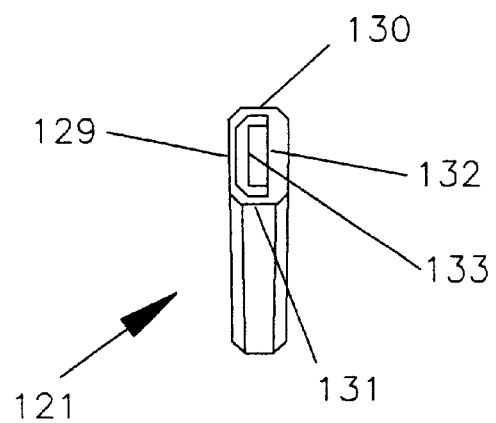
FIG. 19 shows a view looking distally from the proximal end of the handle of FIGS. 17 and 18.
Figure 20:
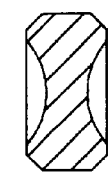
FIG. 20 shows a cross-sectional view along the line 20—20 of FIG. 17.

With reference to FIG. 19, the male coupling half 121 of the handle 111 includes a flat vertical wall 129, top and bottom horizontal walls 130 and 131, and a side wall 132 broken by a recess 133 also seen in FIG. 17 and shown by the phantom line in FIG. 18. The recess 133 is provided for a reason to be described in further detail hereinafter.

Figure 27:
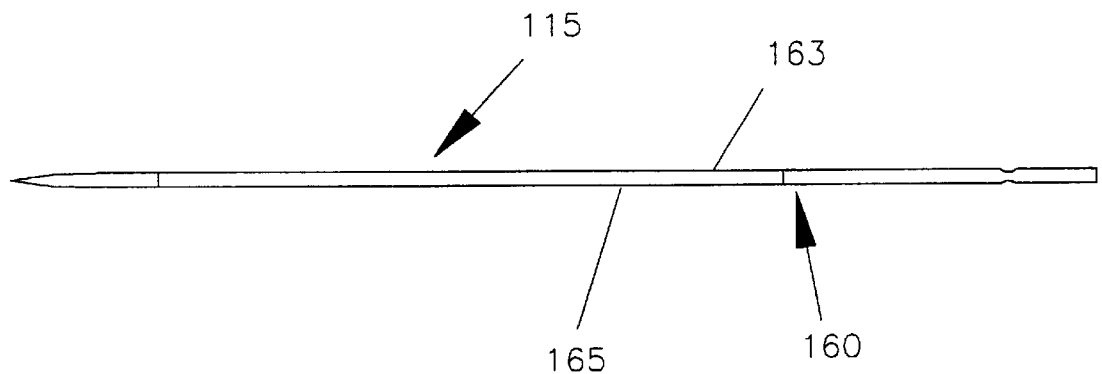
FIG. 27 shows a top view of the blade portion of FIG. 26.
Figure 28:
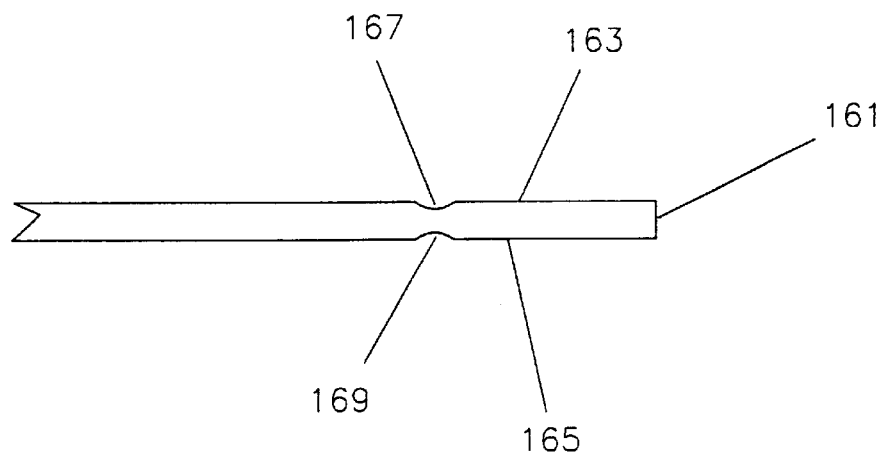
FIG. 28 shows an enlarged top view of the proximal end of the top view of FIG. 27.

With reference to FIGS. 26–28, the blade portion 115 includes a blade having a primary grind 151, a secondary grind 153, and a blade edge 155. These aspects of the blade portion 115 are identical with corresponding structures of the blade portion 15 described with respect to FIGS. 1–15 including all of the details of coatings, materials, angles, etc. The difference between the blade portion 115 and the blade portion 15 lies in the proximal ends thereof. In the blade portion 115, the proximal end thereof is generally designated by the reference numeral 160 and is seen to include a proximal wall 161 as well as side walls 163 and 165. As best seen with reference to FIG. 28, each of the side walls 163 and 165 has a groove therein, 167 and 169, respectively, which grooves extend vertically down the respective walls 163 and 165 as best seen in FIG. 26 with regard to the groove 169. The grooves 167 and 169 are provided for a purpose to be described in greater detail hereinafter.

With reference to FIGS. 24 and 25, a spring clip is generally designated by the reference numeral 170 and is seen to include legs 171 and 173, a connecting portion 175 making the spring clip 170 resemble a "U". As best seen in FIG. 25, the leg 173 has an internally extending rib 177 best understood from FIG. 24 which shows the outer wall 174 of the leg 173 as including an elongated depression 176 also depicted in FIG. 25.

In FIG. 25, the space 179 between the legs 173 and 171 is depicted, in phantom, as receiving the proximal end 160 of the blade portion 115 with the elongated groove 169 thereof receiving the elongated rib 177 of the leg 173. As should now be understood, the blade portion 115 may be received within the space 179 of the spring clip 170 in either of two orientations with the edge 155 facing downwardly or upwardly in the view of FIG. 26, and with the groove 169 receiving the rib 177 in one orientation and with the groove 167 receiving the rib 177 in the other reversed orientation. In either orientation, interaction between the rib 177 and one of the grooves 167, 169 locks the spring clip 170 over the proximal end 160 of the blade portion 115.

With reference back to FIGS. 21–23, it is seen that the fitting 117 has a distal wall 181 through which a slot 183 is formed. The position of the slot 183 with respect to the female coupling half 123 is best seen in FIG. 21. Furthermore, it should also be understood that the recess 133 in the male coupling half 121 of the handle 119 is sized to receive one of the legs 171 or 173 of the spring portion 170 therein.

The preferred manner of using the second embodiment 100 of the present invention will now be explained. First, the spring clip 170 is inserted within the recess 133 in the male coupling half 121 of the handle 119 with the connecting portion 175 facing proximally. With the spring clip 170 so inserted within the recess 133, the handle portion 111 is assembled to the proximal fitting 117 by inserting the male coupling half 121 thereof, with the spring clip 170 inserted within the recess 133, into the female coupling half 123. With the coupling halves so connected, the opening 179 between the legs 171 and 173 is aligned with the slot 183 in the distal face 181 of the proximal fitting 117.

The proximal wall 160 of the blade portion 115 is inserted through the slot 183 with the edge 155 facing either downwardly or upwardly in the view of FIG. 26. When the blade portion 115 has been inserted sufficiently far enough through the slot 183 that either the groove 167 or 169 aligns with the elongated rib 177 of the leg 173 of the spring portion 170, the rib 177 springs into the groove 167 or 169 to thereby lock the blade portion 115 to the handle 111.

After the blade portion 115 has been used and must be replaced, the user may firmly grip the blade portion 115 at any suitable location, preferably above the primary grind 151 in the view of FIG. 26, and with a strong force pull the proximal end 160 of the blade portion 115 out through the slot 183 in the proximal fitting 117. After the surgery, the proximal fitting is removed and the spring clip 170 may either be re-sterilized or discarded and replaced.

As such, an invention has been disclosed in terms of a preferred embodiment thereof which fulfills each and every one of the objects of the invention and provides a new and useful scalpel with a double grind blade edge and detachable handle of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

What is claimed is:

1. A surgical scalpel comprising:

a) a scalpel blade having a proximal end and a distal end, said proximal end having a proximally facing end surface;

b) a plastic connector having a proximal end and a distal end, said connector distal end completely and inseparably surrounding and coupling to said proximal end and proximally facing end surface of said scalpel blade;

c) said proximal end of said connector having a female coupling half including a generally rectangular opening at a proximal termination of said connector and a tapered cavity defined by four walls extending distally from said opening and terminating at a proximally facing coupling surface proximal of said proximally facing end surface of said scalpel blade to define a spacing between said scalpel blade and said cavity, two of said walls tapering toward one another in a distal direction from said proximal termination of said connector;

d) a scalpel handle having a proximal end and a distal end, said distal end of said handle having a tapered male coupling half including four walls having configurations and orientations corresponding to the four walls of said female coupling half, whereby said male coupling half is tightly received within said female coupling half to releasably couple said scalpel blade to said scalpel handle.

2. The scalpel of claim 1, wherein said proximal end and male coupling half of said scalpel handle have axes of elongation defining an angle therebetween of 1°–10°.

3. The scalpel of claim 1, wherein just distal of said rectangular opening, opposed recesses are formed in opposed walls of said female coupling half.

4. The scalpel of claim 3, wherein said male coupling half of said handle includes opposed vertically spaced tangs, each of which includes an outwardly extending bump, each bump being received within one of said recesses formed in opposed walls of said female coupling half to releasably couple said handle to said blade.

5. A surgical scalpel of claim 1, wherein said scalpel blade has a primary grind merging into a secondary grind terminating at a sharp edge, said primary grind being defined by two walls converging at a prescribed angle and said secondary grind being defined by two walls converging at a prescribed angle larger than said prescribed angle of said walls of said primary grind.

6. A surgical scalpel of claim 1, wherein said plastic connector includes external side walls with external ribs extending vertically thereon to permit enhanced gripping of said plastic connector.

7. The scalpel of claim 1, wherein said coupling halves are symmetrical, whereby they may be coupled together in one of two possible orientations with respect to one another.

8. The scalpel of claim 7, wherein said two possible orientations of coupling of said male coupling half with said female coupling half are spaced apart by about 180° about an axis of elongation of said handle.

9. The surgical scalpel of claim 1, wherein said coupling halves are retained together by a frictional snap-fit interconnection between said tapered walls of said female coupling half and correspondingly tapered walls of said male coupling half.

10. The surgical scalpel of claim 1, wherein two of said four walls of said male coupling half taper toward one another in a distal direction.

11. The surgical scalpel of claim 1, wherein said scalpel handle is made of stainless steel.

* * * * *